United States Patent
Lefenfeld et al.

(10) Patent No.: US 7,560,606 B2
(45) Date of Patent: Jul. 14, 2009

(54) TITANIUM OXIDE AND ALUMINA ALKALI METAL COMPOSITIONS

(75) Inventors: Michael Lefenfeld, New York, NY (US); James L. Dye, East Lansing, MI (US)

(73) Assignee: Signa Chemistry, Inc., New York, NY (US)

( * ) Notice: Subject to any disclaimer, the term of this patent is extended or adjusted under 35 U.S.C. 154(b) by 64 days.

(21) Appl. No.: 11/839,684

(22) Filed: Aug. 16, 2007

(65) Prior Publication Data
US 2008/0063596 A1 Mar. 13, 2008

Related U.S. Application Data

(62) Division of application No. 11/232,077, filed on Sep. 22, 2005, now Pat. No. 7,259,128.

(60) Provisional application No. 60/611,700, filed on Sep. 22, 2004, provisional application No. 60/611,701, filed on Sep. 22, 2004.

(51) Int. Cl.
*C01B 3/08* (2006.01)
*C01F 7/02* (2006.01)
*C01G 23/04* (2006.01)
*C07C 15/18* (2006.01)
*C07C 15/28* (2006.01)

(52) U.S. Cl. .................. 585/400; 585/469; 502/344; 502/350; 502/355; 502/415; 502/439; 423/598; 423/610; 423/657

(58) Field of Classification Search ............ 423/598, 423/610, 657; 502/344, 350, 355, 415, 439; 585/400, 469
See application file for complete search history.

(56) References Cited

U.S. PATENT DOCUMENTS 1,665,264 A 4/1928 Holmes et al.
(Continued)

OTHER PUBLICATIONS

K.M. Unruh, T.E. Huber, and C.A. Huber, "Melting and freezing behavior of indium metal in porous glasses," Physical Review B, Sep. 15, 1993, pp. 9021-9027, vol. 48, No. 12, The American Physical Society.
(Continued)

*Primary Examiner*—Cam N. Nguyen
(74) *Attorney, Agent, or Firm*—Nixon Peabody, LLP

(57) ABSTRACT

The invention relates to Group 1 metal/porous metal oxide compositions comprising porous metal oxide selected from porous titanium oxide and porous alumina and an alkali metal or an alkali metal alloy. The compositions of the inventions are described as Stage 0 and I materials. These materials differ in their preparation and chemical reactivity. Each successive stage may be prepared directly using the methods described below or from an earlier stage material. Stage 0 materials may, for example, be prepared using liquid alloys of Na and K which are rapidly absorbed by porous metal oxide under isothermal conditions, preferably at or just above room temperature, to form loose black powders that retain much of the reducing ability of the parent metals. When the low melting Group 1 metals are absorbed into the porous metal oxide at about 150° C., an exothermic reaction produces Stage I material, loose black powders that are stable in dry air. Further heating forms higher stage materials of unknown composition. It is believed that Stage I higher materials represent reductions of the porous metal oxide after absorption of the Group 1 metal. Preferred Group 1 metal/porous metal oxide compositions of the invention are those containing sodium, potassium, or sodium-potassium alloys with sodium and sodium-potassium alloys being most preferred. Each stage of the Group 1 metal/porous metal oxide composition of the invention may be used as a reducing agent reacting with a number of reducible organic materials in the same manner known for alkali metals and their alloys.

12 Claims, 7 Drawing Sheets

U.S. PATENT DOCUMENTS

| | | | |
|---|---|---|---|
| 1,939,647 A | 12/1933 | Arnold et al. | |
| 2,337,419 A | 12/1943 | Sensel | |
| 2,378,290 A | 6/1945 | Drake et al. | |
| 2,731,326 A | 1/1956 | Alexander et al. | |
| 2,740,820 A | 4/1956 | Wilson et al. | |
| 2,765,242 A | 10/1956 | Alexander et al. | |
| 2,816,917 A | 12/1957 | Hansley et al. | |
| 3,033,800 A | 5/1962 | Elliott, Jr. et al. | |
| 3,033,801 A | 5/1962 | Kloepfer et al. | |
| 3,079,234 A | 2/1963 | Jenkins et al. | |
| 3,165,379 A | 1/1965 | Schwartz et al. | |
| 3,274,277 A | 9/1966 | Bloch et al. | |
| 3,290,790 A | 12/1966 | Kunii et al. | |
| 3,322,495 A | 5/1967 | Magee | |
| 3,347,944 A | 10/1967 | Fritz et al. | |
| 3,405,196 A | 10/1968 | Wolff | |
| 3,489,516 A | 1/1970 | Kummerle | |
| 3,493,341 A | 2/1970 | Le Page et al. | |
| 3,507,810 A | 4/1970 | Sanborn et al. | |
| 3,527,563 A | 9/1970 | Shanklin | |
| 3,535,262 A | 10/1970 | Hubbuch et al. | |
| 3,575,885 A | 4/1971 | Hunter et al. | |
| 3,576,891 A | 4/1971 | Rosenthal | |
| 3,577,473 A | 5/1971 | Nagase et al. | |
| 3,658,724 A | 4/1972 | Stiles | |
| 3,670,033 A | 6/1972 | Izawa et al. | |
| 3,679,605 A | 7/1972 | Sanford et al. | |
| 3,793,382 A | 2/1974 | Higuchi et al. | |
| 3,794,712 A | 2/1974 | Aboutboul et al. | |
| 3,801,705 A | 4/1974 | Krekeler et al. | |
| 3,808,152 A | 4/1974 | Nagase et al. | |
| 3,878,289 A | 4/1975 | Beavon | |
| 3,897,509 A | 7/1975 | Nagase et al. | |
| 3,915,995 A | 10/1975 | Holmes et al. | |
| 3,928,485 A | 12/1975 | Nagase et al. | |
| 3,954,896 A | 5/1976 | Shima et al. | |
| 4,087,477 A | 5/1978 | Tazuma et al. | |
| 4,168,247 A | 9/1979 | Hayden et al. | |
| 4,205,192 A | 5/1980 | Harada | |
| 4,229,610 A | 10/1980 | Myers et al. | |
| 4,248,741 A | 2/1981 | Wernli et al. | |
| 4,276,279 A | 6/1981 | Robinson et al. | |
| 4,278,650 A * | 7/1981 | Dorrance | 423/579 |
| 4,313,925 A | 2/1982 | Bamberger | |
| 4,353,815 A | 10/1982 | Antos | |
| 4,366,091 A | 12/1982 | Antos | |
| 4,394,302 A | 7/1983 | Miller et al. | |
| 4,413,156 A | 11/1983 | Watts, Jr. et al. | |
| 4,435,606 A | 3/1984 | Motz et al. | |
| 4,440,631 A | 4/1984 | Togari et al. | |
| 4,446,251 A | 5/1984 | Bartley et al. | |
| 4,471,075 A | 9/1984 | Bartley et al. | |
| 4,508,930 A | 4/1985 | Wideman et al. | |
| 4,633,029 A | 12/1986 | Tillett, Jr. et al. | |
| 4,675,307 A | 6/1987 | Taniguchi et al. | |
| 4,720,601 A | 1/1988 | Suzukamo et al. | |
| 4,727,204 A | 2/1988 | Suzukamo et al. | |
| 4,769,501 A | 9/1988 | Iwahara | |
| 4,837,194 A | 6/1989 | Hayden | |
| 4,975,405 A | 12/1990 | Okamura et al. | |
| 4,982,044 A | 1/1991 | Smith | |
| 5,008,480 A | 4/1991 | Slaugh | |
| 5,128,291 A | 7/1992 | Wax et al. | |
| 5,157,185 A * | 10/1992 | Chu et al. | 585/467 |
| 5,288,935 A * | 2/1994 | Alario et al. | 585/322 |
| 5,292,985 A | 3/1994 | Lattner et al. | |
| 5,856,262 A | 1/1999 | Flick et al. | |
| 6,022,823 A | 2/2000 | Augustine et al. | |
| 6,096,934 A | 8/2000 | Rekoske | |
| 6,315,718 B1 * | 11/2001 | Sharratt | 600/228 |
| 6,358,488 B1 * | 3/2002 | Suda | 423/657 |
| 6,399,528 B1 | 6/2002 | Krell et al. | |
| 6,403,852 B1 | 6/2002 | Yamamoto et al. | |
| 6,492,014 B1 | 12/2002 | Rolison et al. | |
| 6,548,711 B2 | 4/2003 | Yamamoto et al. | |
| 6,586,636 B2 | 7/2003 | Kelly | |
| 6,706,928 B2 | 3/2004 | Kelly | |
| 7,083,657 B2 * | 8/2006 | Mohring et al. | 48/61 |
| 7,315,718 B2 * | 1/2008 | Sisler et al. | 399/297 |

OTHER PUBLICATIONS

J. Monte Russell, Michal Sabat, and Russell N. Grimes, "Organotransition-Metal Metallacarboranes. 59. Synthesis and Linkage of Boron-Functionalized Ferracarborane Clusters," Organometallics, 2002, 21, pp. 4113-4128, American Chemical Society.

Jaacov Levy, Dov Tamarkin, Henry Selig, and Mordecai Rabinovitz, "Potassium Metal Dispersed on Silica: A Versatile Reagent in Organic Chemistry," Angew. Chem. Int. Ed. Engl. 20, 1981, No. 12, p. 1033, Verlag Chemie GmbH, 6940 Weinheim.

Tetsuya Kodaira, Yasuo Nozue, Satoshi Ohwashi, Takenari Goto, and Osamu Terasaki, "Optical Properties of Potassium Clusters Incorporated into Zeolite LTA," Physical Review B, Oct. 15, 1993, pp. 12245-12252, vol. 48, No. 16, The American Physical Society.

V.I. Srdanov, G.D. Stucky, E. Lippmaa, and G. Engelhardt, "Evidence for an Antiferromagnetic Transition in a Zeolite-Supported Cubic Lattice of $F$ Centers," Physical Review Letters, Mar. 16, 1998, pp. 2449-2452, vol. 80, No. 11, The American Physical Society.

Yasuo Nozue, Tetsuya Kodaira, Satoshi Ohwashi, Takenari Goto, and Osamu Terasaki, "Ferromagnetic Properties of Potassium Clusters Incorporated into Zeolite LTA," Physical Review B, Oct. 15, 1993, pp. 12253-12261, vol. 48, No. 16, The American Physical Society.

Andrew S. Ichimura, James L. Dye, Miguel A. Camblor, and Luis A. Villaescusa, "Toward Inorganic Electrides," J. Am. Chem. Soc., 2002, pp. 1170-1171, vol. 124, No. 7, American Chemical Society.

Daryl P. Wernette, Andrew S. Ichimura, Stephanie A. Urbin, and James L. Dye, "Inorganic Electrides Formed by Alkali Metal Addition to Pure Silica Zeolites," Chem. Mater., 2003, pp. 1441-1448, vol. 15, No. 7, American Chemical Society.

V. Petkov, S.J.L. Billinge, T. Vogt, A.S. Ichimura, and J.L. Dye, "Structure of Intercalated Cs in Zeolite ITQ-4: An Array of Metal Ions and Correlated Electrons Confined in a Pseudo-1D Nanoporous Host," Physical Review Letters, Aug. 12, 2002, pp. 075502-1-075502-4, vol. 89, No. 7, The American Physical Society.

Jiliang HE, Dennis D. Klug, Kentaro Uehara, Keith F. Preston, Christopher I. Ratcliffe, and John S. Tse, "NMR and X-ray Spectroscopy of Sodium—Silicon Clathrates," J. Phys. Chem. B, 2001, pp. 3475-3485, vol. 105, No. 17, American Chemical Society.

L. F. Fieser, M. Fieser, "Topics in Organic Chemistry". (Reinhold, New York, 1963) pp. 514-515.

A. Wurtz, "Ueber eince neue Klasse organischer Radicale; nach" Justus Liebig Ann. Chem. 96, 364-375 (1855).

P. P. Edwards, P. A. Anderson, J. M. Thomas, "Dissolved Alkali Metals in Zeolites" Accounts of Chemical Research 29, 23-29 (1996).

J. A. Rabo, P. H. Angell, P. H. Kasai, V. Schomaker, Studies of Cations in Zeolites: Adsorption of Carbon Monoxide; Formation of Ni ions and Na$_{3/4}^+$ centres, Discussions of the Faraday Society 41, 328-349 (1966).

P. A. Anderson, D. Barr, P. P. Edwards, "Solvated Electrons in the Synthesis of Ionic Clusters in Zeolites" Angewandte Chemie International Edition in English 11, 1501-1502 (1991).

R. Qadeer, S. Akhtar, F. Mahmood, "Nitrogen Adsorption On Metal Impregnated Alumina by Continuous Flow Method" Back to Journal of IAS, vol. 8, No. 4, 1995.

International Search Report dated Jan. 6, 2006.
International Search Report dated Mar. 15, 2006.

* cited by examiner

TITANIUM OXIDE AND ALUMINA ALKALI METAL COMPOSITIONS

RELATED APPLICATION DATA

This application is a divisional of U.S. patent application Ser. No. 11/232,077, filed Sep. 22, 2005, which claims benefit of priority of Provisional Application Ser. Nos. 60/611,700 and 60/611,701, both filed on Sep. 22, 2004, the entire disclosures of which are incorporated herein by reference.

FIELD OF THE INVENTION

The invention relates to porous metal oxide compositions made by interaction of alkali metals or alloys of these metals with porous titanium oxide or porous alumina. The compositions have improved handling characteristics and retain the reactivity of the neutral alkali metal or alloy.

BACKGROUND OF THE INVENTION

Alkali metals, those in Group 1 of the periodic table, and alloys of alkali metals, are very reactive in their metallic, or neutral, state. The alkali metals and their alloys are very reactive toward air and moisture and may catch fire spontaneously when exposed to these agents. To avoid the inherent hazards associated with their activity, the neutral metal or alloy must often be stored in vacuo or under an inert liquid such as oil in order to protect it from contact with the atmosphere, which may result in oxidation or other reactions. For example, sodium metal is often stored in Nujol oil which must, to avoid unwanted impurities, be removed prior to use in chemical reactions. This places severe restrictions on its shipment and use.

The combination of alkali metals with silica zeolites, such as ZSM-5, has been extensively studied in many laboratories. For example, it was recently shown that pure silica zeolites can absorb up to 12 mole percent cesium from the vapor phase and comparable amounts of the other alkali metals (except lithium). Prior research with alkali metal encapsulation in all-silica zeolites revealed that such a combination reacts exothermically with water to produce hydrogen quantitatively. (See, for example, "Toward Inorganic Electrides", A. S. Ichimura, J. L. Dye, M. A. Camblor and L. A. Villaescusa, *J. Am. Chem. Soc.*, 124, 1170-1171 (2002) and "Inorganic Electrides Formed by Alkali Metal Addition to Pure Silica Zeolites", D. P. Wernette, A. S. Ichimura, S. A. Urbin and J. L. Dye, *Chem. Mater.* 15, 1441-1448, (2003). The concentration of sodium absorbed by the zeolite compositions, however, was too low to be practical. In addition, the reaction was relatively slow with slow sodium diffusion within the limited zeolite pore size.

The use of potassium metal dispersed on silica as a reagent in organic synthesis has been reported by Levy et al., Angew. Chem. Int. Ed. Engl. 20 (1981) p. 1033. Potassium metal was dispersed onto silica gel (CAS Registry No. 7631-86-9: actually colloidal silica, which has no internal surface area) producing an amorphous material. The reactivity of the material was demonstrated with water and benzophenone, as shown below. See also, Russel, et al., Organometallics 2002, 21, 4113-4128, Scheme 3.

It has been reported to disperse sodium on titanium dioxide ($TiO_2$) to readily reduce zinc chloride leading to a highly active zinc powder which inserts into secondary alkyl and benzylic bromides under mild conditions, producing the corresponding zinc reagents in high yield. (See Heinz Stadtmuller, Bjorn Greve, Klaus Lennick, Abdelatif Chair, and Paul Knochel, "Preparation of Secondary Alkyl and Benzylic Zinc Bromides Using Activated Zinc Metal Deposited on Titanium Dioxide" *Syntheis*, 1995, 69-72.). According to Stadtmuller, it was observed that residual water content in the support has a detrimental effect. For this reason, solid supports like barium, tin, or alumina, as well as silica, could not be used. Commercial $TiO_2$ is almost water free and constitutes the best support for this purpose. Thus the addition of sodium (ca. 8 g/100 g $TiO_2$) to $TiO_2$ (dried at 150° C. for 2 hrs) at 150° C., produces a homogenous, gray powder after 15 min. This powder is not pyrophoric but its exposure to air and moisture results in a slow decomposition (2-3 min).

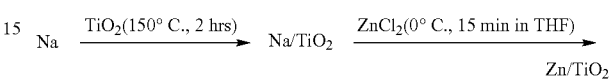

Stadtmuller's experiment was as follows. A 3-necked 100 mL flask equipped with Ar inlet, a glass stopper, and a septum cap was charged with $TiO_2$ (18 g, 380 mmol) and heated for 2 hr at 150° C. under vacuum (0.1 mmHg). The glass stopper was replaced with a mechanical stirrer, the reaction flask was flushed with Ar and Na (1.50 g, 65 mmol) was added at once. Alternatively, the Na could be added at 25° C. to the dry $TiO_2$. The reaction mixture was vigorously stirred at 150° C. for 15 min and cooled to 0° C. leading to a gray homogenous powder. A solution of dry $ZnCl_2$ (4.57 g, 35.5 mmol) in THF (20 mL) was added with stirring. After 15 min., the activated Zn on $TiO_2$ was ready to use.

Sterling E. Voltz, in "The Catalytic Properties of Supported Sodium and Lithium Catalysts" *J. Phys. Chem.*, 61, 1957, 756-758, investigated the catalytic properties of supported alkali metal catalysts for hydrogen-deuterium exchange and ethylene hydrogenation. Sodium dispersed on dried alumina does not increase the activity of the alumina for hydrogen-deuterium exchange. However, hydriding the sodium-alumina greatly increases the exchange activity, the hydrided catalyst being active even at −195° C. Sodium-silica catalysts are much less active than the corresponding sodium-alumina catalysts. Supported sodium and lithium catalysts are also active for ethylene hydrogenation even below room temperature; in this case, however, hydrogen treatments have relatively minor effects on the activities. The supported alkali metal catalysts are much more active than the bulk hydrides of sodium and lithium for both of these reactions. The major role of the support is probably to increase the effective area of the alkali metal. The results of this study suggest that the mechanisms of activation of hydrogen and ethylene on alkali metal hydrides are similar to those previously postulated for alkaline earth metal hydrides. The activations probably occur at metal sites at metal-metal hydride interfaces. The results obtained with the bulk hydrides suggest that hydrogen activation takes place more readily at lithium sites than at sodium sites, and the reverse situation is likely for ethylene activation.

Voltz's experiment was as follows. The supported sodium and lithium catalysts were prepared by dispersing the molten metal over powdered alumina or silica which had been dried by evacuation at 500° C. for about 16 hours. In a typical preparation (sodium-alumina) the dried alumina and sodium were placed in a high vacuum reactor equipped with a magnetic stirrer. Transfers of materials to the reactor were made in a dry box in dry nitrogen. The reactor was heated lowly under evacuation while the solids were stirred. When the sodium melted, it dispersed over the alumina powder. The reactor was heated to about 150° C. and kept at this temperature (under evacuation and with stirring) for at least one-half hour. Small amounts of gaseous products were given off in some preparations when the molten alkali metal dispersed over the powder. In the preparation of lithium-alumina catalysts, the reactor was heated to about 280° C. because of the higher melting point of lithium (186° C.).

Morevoer, Alois Furstner and Gunter Seidel, in "'High-Surface Sodium' as a Reducing Agent for $TiCl_3$," *Synthesis*, 1995, 63-68, disclosed that sodium deposited on inorganic supports such as $Al_2O_3$, $TiO_2$, and NaCl ('high-surface sodium') is a cheap, readily prepared, nonpyrophoric reducing agent for $TiCl_3$. The low-valent Ti thus obtained, after only 1 hr. reduction time, is well suited for McMurry coupling reactions, particularly of aromatic carbonyl compounds. It exhibits a previously unrivalled template effect for the cyclization of dicarbonyl compounds to (macrocyclic) cycloalkenes and is suitable for the reduction of N-acyl-2-aminobenzophenone derivatives to 2,3-disubstituted indoles.

In this regard, $Na/Al_2O_3$ can be conveniently prepared in two different ways as a homogenous grey, nonpyrophoric powder (method A: mixing/grinding of $Al_2O_3$ and Na at 180-190° C.; method B: deposition of melting Na on $Al_2O_3$ suspended in boiling toluene by means of an Ultra turrax stirrer). With ~4 mmol Na per g of reagent (10% metal content w/w), the available surface area of the alumina is well exploited without risking any severe overloading.

Furstner's experiment was as follows.

Method A: Na sand (10 g; 1-2 mm) was added in portions during 30 min to predried $Al_2O_3$ (100 g) with good mechanical stirring under Ar at 180-190° C. This afforded $Na/Al_2O_3$ as a grey-black, air-sensitive but nonpyrophoric powder which can be stored for extended periods of time under Ar at RT without loss of activity. According to Furstner, this simple procedure is less appropriate for the preparation of $Na/TiO_2$ and Na/NaCl for reasons of insufficient mixing.

Method B: To a vigorously stirred suspension of predried $Al_2O_3$ (100 g) in boiling Toluene (350 mL) was added Na sand (10 g) over a period of 20 min. Stirring and reflux were continued for another 15 min, the mixture was cooled to RT, filtered under Ar, washed with pentane (ca. 300 mL in several portions) and dried in vacuo. For the preparation of $Na/TiO_2$, a larger volume of toluene (~800 mL) was required to achieve good agitation. Id.

In addition, U.S. patent application Ser. No. 10/995,327 filed Nov. 24, 2004 and entitled "SILICA GEL COMPOSITIONS CONTAINING ALKALI METALS AND ALKALI METAL ALLOYS" describes silica gel compositions made by interaction of alkali metals or alloys of these metals with silica gel, and is hereby incorporated by reference.

A need exists, therefore, to have alkali metals and their alloys available in a form that may be easily handled without a significant loss in metal reactivity. This invention answers that need.

SUMMARY OF THE INVENTION

The invention relates to a Group 1 metal/porous metal oxide composition comprising the product of mixing a liquid Group 1 metal or alloy with a porous metal oxide selected from porous titanium oxide and porous alumina in an inert atmosphere under isothermal conditions near ambient temperatures sufficient to absorb the liquid Group 1 metal or alloy into the porous metal oxide pores. The Group 1 metal/porous metal oxide composition produced reacts with dry $O_2$. This material is referred to as "Stage 0" material.

The invention also relates to a Group 1 metal/porous metal oxide composition comprising the product of mixing a Group 1 metal or alloy with porous metal oxide selected from porous titanium oxide and porous alumina under exothermic conditions that may be above ambient temperatures sufficient to absorb the Group 1 metal or alloy into the porous metal oxide pores. The Group 1 metal/porous metal oxide composition produced does not react with dry $O_2$. This material is referred to as "Stage I" material.

The invention also relates to a Group 1 metal/porous metal oxide composition comprising the product of mixing a liquid Group 1 metal or alloy with porous metal oxide under conditions sufficient to absorb the liquid Group 1 metal or alloy into the porous metal oxide pores and heating the resulting mixture to a temperature of about 150° C. or higher. The Group 1 metal/porous metal oxide composition produced does not react with dry $O_2$.

The invention further relates to a method for producing hydrogen gas comprising the step of contacting any of the Group 1 metal/porous metal oxide compositions described herein with water. Also, the invention relates to a reduction reaction of an organic compound in the presence of an alkali metal, the improvement comprising conducting the reaction in the presence of any of the Group 1 metal/porous metal oxide compositions described herein. The reduction reactions may include, for example, dehalogenation reactions and Wurtz reactions.

In addition, the invention relates to a method of drying an organic solvent comprising the step of contacting an organic solvent with porous alumina for a sufficient time to remove water from the solvent. The contacting step may be done by batch or through a column.

DETAILED DESCRIPTION OF THE INVENTION

Figure 1:
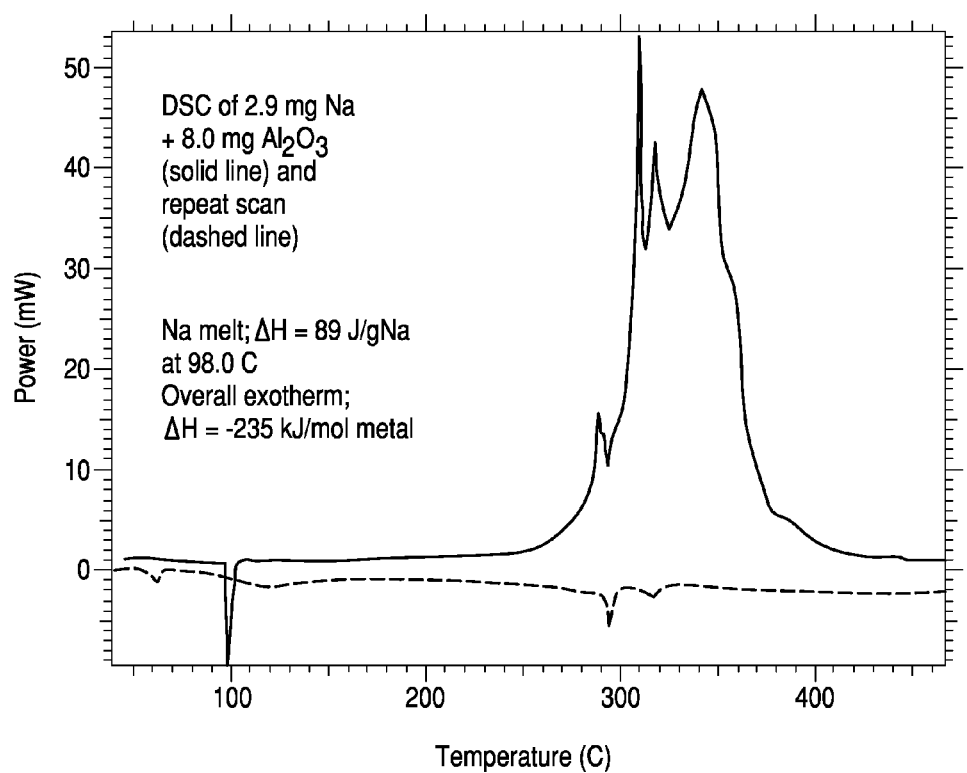
FIG. 1 shows a Differential Scanning Calorimetry (DSC) trace for a mixture of 2.9 mg of Na metal with 8.0 mg of porous $Al_2O_3$.

Group 1 Metals: Alkali Metals and Alkali Metal Alloys

Alkali metals are those metals in the Group 1 family of the periodic table. The terms "Group 1 metal" or "Group 1 metals" are used here to describe alkali metals and alloys of alkali metals which may be used in the porous metal oxide compositions of the invention. Those alkali metals include sodium (Na), potassium (K), rubidium (Rb), and cesium, (Cs). Of these alkali metals, sodium and potassium are preferred for use in the porous metal oxide compositions of the invention, with sodium being particularly preferred.

Alkali metal alloys may also be used in the porous metal oxide compositions of the invention. The alkali metal alloy is preferably an alloy of two or more alkali metals, for example sodium-potassium (e.g. NaK or $Na_2K$) alloys, which are particularly preferred. Other preferred alkali metal alloys are those containing, potassium, cesium, and rubidium with each other and particularly alloys of these elements with sodium. The alkali metal alloys are within the "Group 1 metal" definition as used in the specification and claims.

In preparing the Group 1 metal/porous metal oxide compositions of the invention, the Group 1 metal is typically mixed with the porous metal oxide, porous titanium oxide or porous alumina. The viscosity of the liquid Group 1 metal should be at least low enough to be absorbed into the pores of the porous titanium oxide or porous alumina. One method to accomplish this is heating the alkali metal in an inert atmosphere prior to mixing it with the porous metal oxide. Alternatively, depending on the stage of material to be prepared, the Group 1 metal may be mixed as a solid with the porous metal oxide and the mixture heated to melt the alkali metal.

Another method to introduce Group 1 metals into porous metal oxide is from the vapor phase as was done with zeolites. (See A. S. Ichimura, J. L. Dye, M. A. Camblor and L. A. Villaescusa, *J. Am. Chem. Soc.*, 124, 1170-1171 (2002) and D. P. Wemette, A. S. Ichimura, S. A. Urbin and J. L. Dye, *Chem. Mater.* 15, 1441-1448, (2003).). In another method, a Group 1 metal can be deposited onto the porous metal oxide from a metal-ammonia solution. (See M. Makesya and K. Grala, Syn. Lett. 1997, pp. 267-268, "Convenient Preparation of 'High Surface Sodium' in Liquid Ammonia: Use in Acyloin Reaction."). The metal-ammonia solution can be used to avoid agglomeration of the metal in upon mixing with the porous metal oxide and to prepare an intimate mixture of the metal with the porous metal oxide. However, in practice the metal-ammonia solution method of mixing Group 1 metals with porous metal oxide was accompanied by considerable decomposition of the metal-ammonia solution to form amides. However, as preferred for the invention, simply allowing the liquid Group 1 metal to contact the porous metal oxide avoids the time-consuming vapor deposition or metal-ammonia routes.

As discussed below, for at least Stage 0 material, it is generally preferred that the Group 1 metal have a melting point within about 15° C. of room temperature (approximately 25° C.). For example cesium and rubidium have melting points of 28.5° C. and 38.5° C., respectively. Typically alloys of the two or more alkali metals are, and preferably are, liquid at or near room temperature. A preferred low-melting alloy is that between sodium and potassium (NaK) at various molar ratios of Na to K between 0.5 and 3.0, more preferably with a 2:1 molar ratio, i.e. $Na_2K$. All Na—K alloys with mole ratios between 0.5 and 2.5 begin melting at a eutectic melting temperature of −12.6° C. Melting is complete at 25° C. for mole ratios of about 0.12 and 3.1. Other binary alloys of the alkali metals, such as Cs with Rb, K, or Na and Rb with Na or K also melt below, or only slightly above room temperature and would therefore be appropriate to use for this purpose. Ternary alloys, made from three of these four alkali metals, or an alloy of all four would also melt at low enough temperatures to form a Group 1 metal/porous metal oxide composition of the invention.

Porous Metal Oxides

The porous metal oxide powders used in this invention are porous titanium oxides and porous alumina. Any porous titanium oxide may be used, including TiO, $TiO_2$, $Ti_2O_3$, and $Ti_3O_5$. Given their porous natures, these porous metal oxides can take up large amounts of absorbed material. Unlike prior adsorption of alkali metals onto titanium oxide or alumina powders, the compositions of the invention absorb the alkali metals into the pores of porous titanium oxides and porous alumina. Porous titanium oxides and porous alumina are difference that the more familiar non-porous forms such as colloidal titanium oxides and colloidal alumina. Porous titanium oxides may be purchased from Sachtleben Chemie, and porous alumina may be purchased from Almatis AC.

The porous metal oxides used in the porous metal oxide compositions of the invention preferably have pore sizes ranging from 50 Å to 1000 Å. More preferably, the pore size may range from 100 to 300 Å. Even more preferably, the average diameter of the pores of the porous metal oxide will be approximately 150 Å.

Although porous metal oxides, when purchased, are free-flowing powders, they typically contain large amounts of gaseous material, such as water and air. These are preferably removed prior to mixing the porous titanium oxide or porous alumina with an alkali metal or alloy to form compositions of the invention. The porous metal oxide may be de-gassed using methods known in the art. For example, to remove the gaseous material the porous metal oxide may be heated under vacuum in an evacuable flask, first with a hot air dryer and then with a torch. Such heating achieves temperatures of approximately 300° C. It is also possible, and is actually preferred, to remove the gases more easily and to passivate active sites by heating the porous metal oxide to 600° C. or hotter (900° C.) in air (calcination). The porous metal oxide is typically cooled to room temperature before preparing a Group 1 metal/porous metal oxide composition of the invention.

Porous Metal Oxide Compositions Containing Alkali Metal and Alkali Metal Alloys

The ability to utilize alkali metals or their equivalents in a convenient form continues to be a need in the chemical industry and for the hydrogen production community. Answering that need, the invention relates to Group 1 metal/porous metal oxide compositions comprising a porous metal oxide selected from porous titanium oxide and porous alumina and an alkali metal or an alkali metal alloy. The compositions of the inventions that utilize titanium oxide or porous alumina are described as Stages 0 and I materials. These materials differ in their preparation and chemical reactivity. Stage I may be prepared directly using the methods described below from an earlier preparation of Stage 0 material. Stage 0 materials may, for example, be prepared using liquid alloys of Na and K which are rapidly absorbed by porous titanium oxide or porous alumina under isothermal conditions, preferably at or just above room temperature, to form loose black powders that retain much of the reducing ability of the parent metals. It is believed the Stage 0 materials have small clusters of neutral Group 1 metal absorbed in the porous metal oxide pores. The Stage 0 materials are pyrophoric but less explosive in air compared to their parent Group 1 metal. Stage I materials may be prepared by heating Stage 0 materials at 150° C. overnight. Stage I material is a loose black powder that is stable in dry air. Further heating above 200° C. causes an exothermic reaction to produce another stage or stages. It is believed that Stage I and the materials formed at higher temperatures represent reductions of the porous metal oxide after absorption of the Group 1 metal. Preferred Group 1 metal/porous metal oxide compositions of the invention are those containing sodium, potassium, or sodium-potassium alloys with sodium and sodium-potassium alloys being most preferred.

As described below, a number of samples of this material with $Na_2K$, at various loads and mass ratios, were tested by Differential Scanning Calorimetry (DSC). The heat absorbed upon melting $Na_2K$ in the porous metal oxide pores at −25-0° C. was used to determine the amount of encapsulated metal that remained as metal in the porous metal oxide. This was followed by broad exothermic peaks between 5° C. and 450° C. Upon cooling and reheating the same sample, no appreciable thermal peaks were observed. This shows that the heat treatment causes encapsulated metal in the pores to react with porous metal oxide to produce new materials, although the boundaries are not sharp. This conversion does not appreciably change the hydrogen producing abilities of the material.

The Group 1 metal/porous metal oxide compositions of the invention comprise porous metal oxide selected from porous titanium oxide and porous alumina with absorbed Group 1 metal. The amount of Group 1 metal loading is dependent upon the pore size and pore density of the actual porous metal oxide used. Typically, the Group 1 metal may be present in the compositions of the invention up to about 30% by weight. Preferably, the amount of metal ranges from 25% to 30% by weight. In the Stage I materials of the invention, loadings above about 30% by weight result in some free metal remaining in the porous metal oxide pores or on the surface.

The Stage 0 and Stage I metal/porous metal oxide compositions of the invention react rapidly with water to produce gaseous hydrogen. In the case of Stage I metal/porous alumina the yield is nearly quantitative, typically about 90-95%. However in the case of Stage 0 and Stage I metal/porous titanium oxide, the yield was lower. About 10% of the added metal did not evolve hydrogen when water was added. Apparently the metal reacted with the porous titanium oxide to produce a product that did not react with water to produce hydrogen. The Group 1 metal/porous metal oxide compositions of the invention, whose preparation and properties are described below, show promise as easily shipped and handled sources of clean hydrogen and as powerful reducing agents for a variety of reactions of organic compounds. Table I below summarizes the preparation processes and uses of Stage 0 and I materials.

oxide, and minimize defect sites. Other methods known in the art to dry, de-gas and/or passivate the porous metal oxide may also be used.

Stage 0 Material

The Stage 0 material of the invention apparently contains low-melting Group 1 metals absorbed into the pores of porous metal oxide without reaction (except for the partial reaction with porous titanium oxide described above). Thus, Stage 0 material can be viewed as nanoscale alkali metal or alkali metal alloy particles absorbed in the open pores and channels within the porous metal oxide. The Stage 0 material of the invention is a Group 1 metal/porous metal oxide composition comprising the product of mixing a liquid Group 1 metal or a liquid Group 1 metal alloy, such as $Na_2K$, with porous titanium oxide or porous alumina under isothermal conditions sufficient to absorb the liquid Group 1 metal or liquid Group 1 metal alloy into the porous metal oxide pores. Preferred Group 1 metals for Stage 0 materials include a low-melting Group 1 metal such as cesium or a NaK alloy. The Stage 0 Group 1 metal/porous metal oxide composition of this invention reacts with dry $O_2$, which differentiates it from Stage I materials. Since Stage 0 material is reactive with dry air, it should be handled in vacuo, in an oxygen-free atmosphere, and preferably in an inert atmosphere, such as under nitrogen or an inert gas. While the Stage 0 material will ignite spontaneously in air, it can be stored in a closed container, e.g. a screw-top vial.

To form Stage 0 materials, a Group 1 liquid metal or alloy is mixed with porous titanium oxide or porous alumina in an inert atmosphere under isothermal conditions, preferably at room temperature or slightly above, for a time sufficient to permit the alkali metal or alloy to be absorbed into the silica. The mixing must be done in an inert atmosphere such as within a glove box or glove bag. During formation of a preferred Stage 0 material, a liquid Group 1 metal, such as $Na_2K$, may be poured over a bed of porous metal oxide at room temperature. The mixture is agitated, preferably stirred or shaken, to achieve good mixing. The liquid Group 1 metal is

TABLE I

Summary of Stages 0 and I

| Material Type | Preferred Metals/ Alloys Used | Preparation Procedures |
|---|---|---|
| Stage 0 | Liquid alloys ($NaK_2$, NaK, $Na_2K$, etc.) | Under inert atmosphere or vacuum, liquid alkali metal alloy is added to porous metal oxide at or near room temperature. On a large-scale, this process would be best done by adding the liquid metal or alloy to porous metal oxide slowly with stirring and cooling to dissipate any heat which may be produced. |
| Stage I from Stage 0 | Liquid alloys (NaK, $Na_2K$, etc.) Liquid single metals (Cesium, Rubidium) | Under inert atmosphere or vacuum, Stage 0 material is heated with mixing to at least 150° C. long enough to complete the conversion. |
| Stage I from solid Group 1 metals | Sodium, Potassium | Under inert atmosphere or vacuum, solid alkali metal is added to porous metal oxide and is heated with mixing to at least 150° C. to incorporate all metal. |

As discussed above, to prepare all of the Group 1 metal/porous metal oxide compositions of the invention, it is preferred to de-gas and passivate the porous titanium oxide or porous alumina prior to mixing it with the Group 1 metal. Typically, in preparing the materials of the invention, the porous metal oxide is initially heated to approximately 600° C. or higher in air to remove water, de-gas the porous metal preferably absorbed into the porous metal oxide without any significant heat of reaction or appreciable release of heat. At larger scales, the alkali metal is preferably added slowly to avoid any exothermicity due to alkali metal absorption into the pores of the porous metal oxide.

Depending upon the Group 1 metal used, the absorption of the liquid Group 1 metal to form Stage 0 material preferably occurs within 15° C. of room temperature (25° C.). In the typical process, so little heat is evolved that the sample does not become noticeably warm but converts to a product which is a free-flowing amorphous black powder, in which the individual particles have a shiny surface. The mixture is agitated for a time sufficient to allow the alkali metal or alloy to be absorbed or "soaked up" into the pores of the porous titanium oxide or porous alumina. The time of mixing generally depends upon the batch size of material being prepared and may range from several minutes to several hours. This mixing time holds true for the preparation of any Group 1 metal/porous metal oxide composition of the invention.

When preparing Stage 0 material, any heat generated by the reaction or put into the reaction should be controlled or dissipated. A significant temperature increase during the preparation should be avoided. In a preferred embodiment, the Stage 0 material is formed at ambient temperature, e.g. near room temperature (25° C.). Heating much above this temperature generally leads to the formation of Stage I material. The temperature may be controlled by spreading the porous metal oxide (for example, on a metal tray), stirring the porous metal oxide, or by cooling the reaction vessel. The reaction temperature should, however, be maintained such that the Group 1 metal remains liquid so that it may be absorbed by the porous titanium oxide or porous alumina. It should also be noted that Stage 0 material might slowly convert to Stage I material over time when kept at room temperature, although further conversion to higher stage material does not occur without heating as discussed below.

The Stage 0 material is a shiny black powder that reacts exothermically with water. A DSC of the Stage 0 material made with alumina shows the presence of the alkali metal in its neutral state within the porous metal oxide. This endothermic melting signal was not observed with Stage 0 Group 1 metal/porous titanium oxide. While the exact composition of the Stage 0 material is not currently known, the melting point of metals within the Stage 0 material is lower than the melting point of the most common Group 1 alloys, such as $Na_2K$, thus indicating that small particles of the Group 1 alloys are within the pores of the porous metal oxide.

The Stage 0 materials are the most reactive members of the Group 1 metal/porous metal oxide compositions of the invention. Since the addition of a low-melting alkali metal or alloy to porous titanium oxide or porous alumina produces a Stage 0 material without significant heat evolution, the Stage 0 material retains most of the reducing ability of the alkali metal. Because of their reactivity toward air and moisture they must be handled with care and not allowed to come in contact with large amounts of air and moisture. In spite of these restrictions, the Stage 0 materials have utility in highly reducing chromatography applications. The porosity of packed columns of the Group 1 metal/porous metal oxide compositions of the invention provide a reducing environment that cannot be met with the parent metals or alloys. This, as discussed below, permits the Stage 0 material to be used to produce hydrogen from water and as a reducing agent reacting with a number of reducible organic materials in a manner similar to that of the pure alkali metals.

Stage I Material

The Stage I material of the invention is a Group 1 metal/porous metal oxide composition comprising the product of heating the Stage 0 material or mixing a solid Group 1 metal with porous titanium oxide or porous alumina and heating the mixture above the melting temperature of the metal in order to absorb the Group 1 metal into the porous metal oxide pores. The Stage I Group 1 metal/porous metal oxide composition produced does not react with dry $O_2$. In the Stage I material it appears that the alkali metal or alloy has been converted to a form that loses the properties of the bulk metal, such as melting.

The Stage I material of the invention may be formed by mixing the liquid Group 1 metal, at or just above its melting point with porous titanium oxide or porous alumina under an inert atmosphere to allow the Group 1 metal to be absorbed into the pores of the porous metal oxide. The Group 1 metal may also be mixed with the porous metal oxide using one of the alternative methods discussed above, such as adding the Group 1 metal as a vapor. The mixture is then maintained at or slightly above the melting point of the Group 1 metal (i.e., approximately 70° C. to 150° C.) and agitated for between several minutes to several hours. Generally speaking, higher reaction temperatures convert the material in shorter times. The reaction to form Stage I materials is mildly exothermic, and, on a large scale, the process would be preferably done by adding the liquid metal or alloy to the porous metal oxide with continual mixing, in such a way as to remove heat as it is produced. The reaction appears to form an alkali metal—porous metal oxide lattice. The exothermic nature of the reaction differentiates Stage I material from Stage 0 material. Heating above the exotherm can convert Stage I material to higher stage materials, depending upon the temperature.

When low-melting Group 1 metals are added to calcined and outgassed porous metal oxide in a closed environment such as an Erlenmeyer flask, the system often becomes warm because of exothermic reactions between the alkali metal and the porous metal oxide or its defect sites. This can result in the formation of mixtures of Stages 0 and I. The simplest and most direct preparation of Stage I materials is to heat Stage 0 samples overnight under an inert atmosphere at temperatures of 150° C. Other times and temperatures may work also, but care should be taken to avoid overheating, which can lead to the formation of higher stage materials. To insure a homogeneous product, provision should be made for agitation during the heating process.

The Stage I material is an amorphous, black powder that does not immediately react with dry air, but reacts exothermically with water. A DSC of the Stage I material shows little or no Group 1 metal remaining within the porous metal oxide. The difference between Stages I and 0 is that the former can be handled in dry air and even quickly transferred in ordinary laboratory air without catching fire or degrading rapidly. When kept under an atmosphere of dry oxygen for hours to days, Stage I material (in contrast to Stage 0 material, which reacts which dry $O_2$) is unchanged and produces the same amount of hydrogen gas upon reaction with liquid water as do fresh samples.

Stage I material has many uses in reactive chemistry as an active reducing agent, and for hydrogen production.

Thermal Behavior

Group 1 metals react exothermically with the porous metal oxide compositions of the invention. The Differential Scanning Calorimetry (DSC) trace shown in FIG. 1 for a mixture of 2.9 mg of solid sodium metal and 8.0 of porous alumina ($Al_2O_3$) in the DSC pan has a sodium melting endotherm at 98° C. ($\Delta H=89$ J/g Na) followed at 280-380° C. by a multiple exotherm with $\Delta H=-235$ kJ per mole of Na. This is so large that it must represent a chemical reaction between Na and $Al_2O_3$. The dashed line is a repeat scan that shows no major thermal peaks. In FIG. 1, the solid line represents the first scan, and the dashed line represents a repeat scan.

Figure 2:
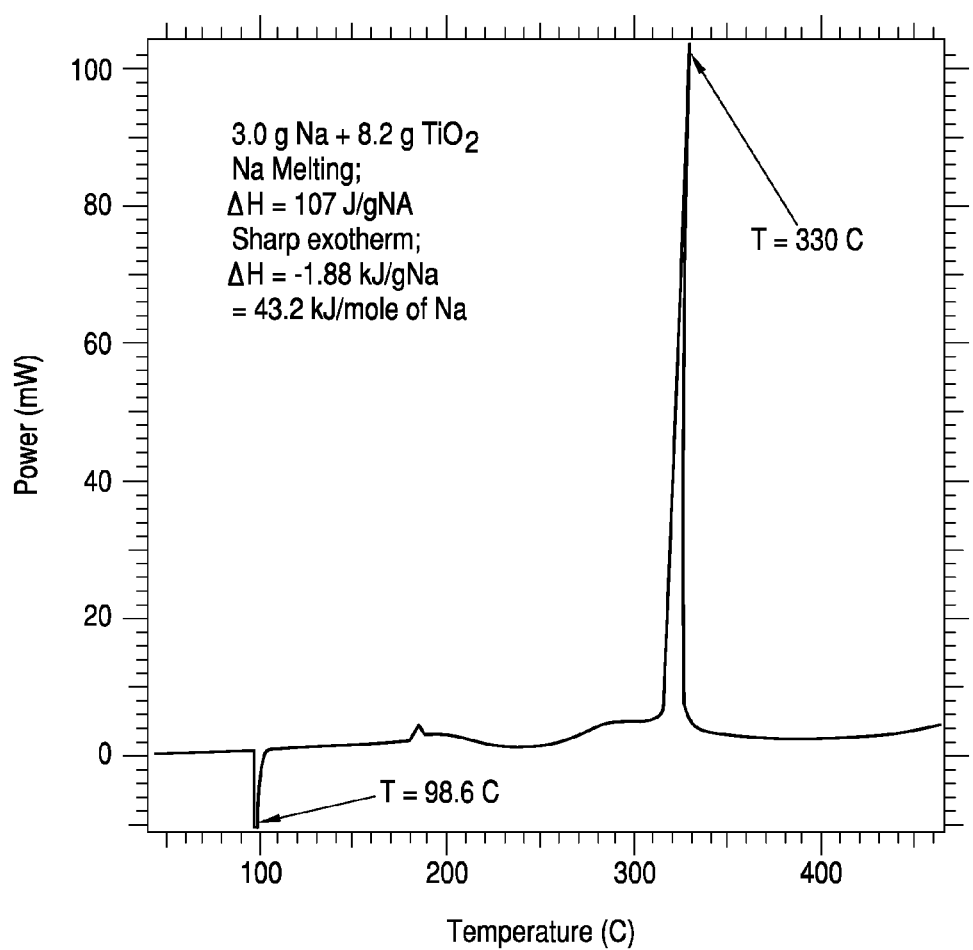
FIG. 2 shows a Differential Scanning Calorimetry (DSC) trace for a mixture of 3.0 mg of Na metal with 8.2 mg of porous $TiO_2$.

FIG. 2 shows a Differential Scanning Calorimetry (DSC) trace for a similar mixture of 8.2 mg of porous titanium dioxide ($TiO_2$) and 3.0 mg of Na metal in the DSC pan. The DSC trace shows the Na melting endotherm at 98° C.

($\Delta H=107$ J/g Na) followed at 330° C. by an exotherm with $\Delta H=-43.2$ kJ per mole of Na ($\Delta H=-1.88$ kJ/g Na). Thus, we presume that the exothermic peaks observed with various Group 1 metal/porous metal oxide compositions in the DSC traces shown in FIGS. 3-6 represent similar reduction reactions.

Figure 3:
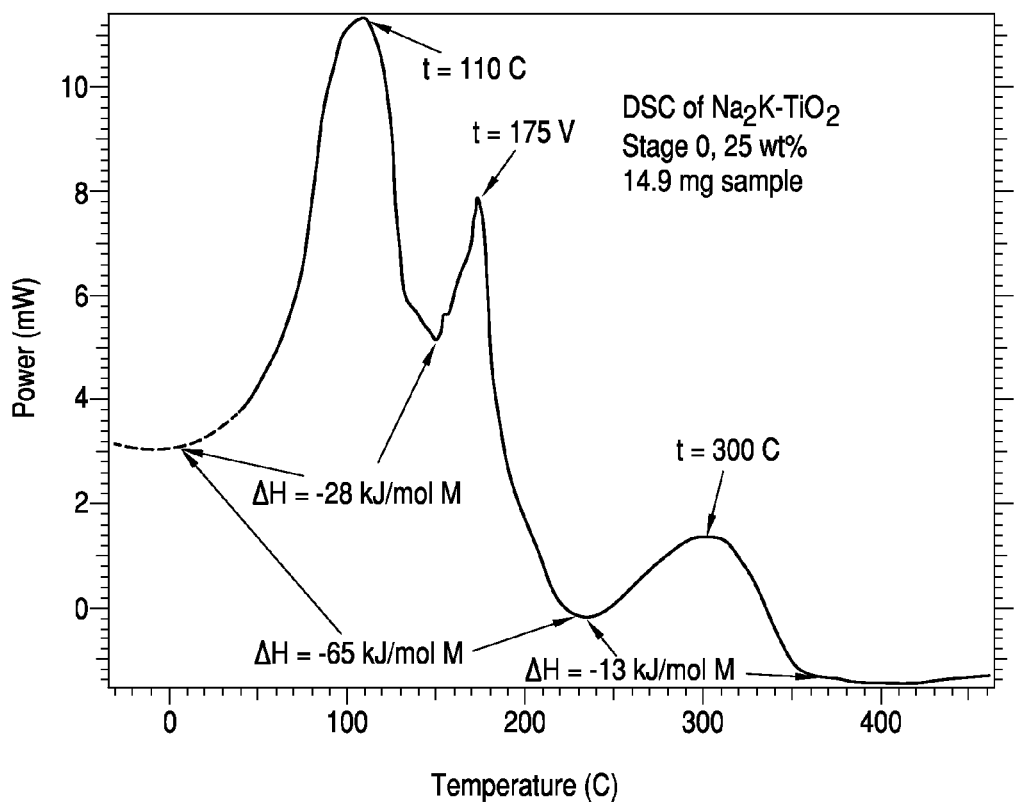
FIG. 3 shows a Differential Scanning Calorimetry (DSC) trace for a 14.9 mg sample of Stage 0, 25 wt % $Na_2K$—$TiO_2$.
Figure 4:
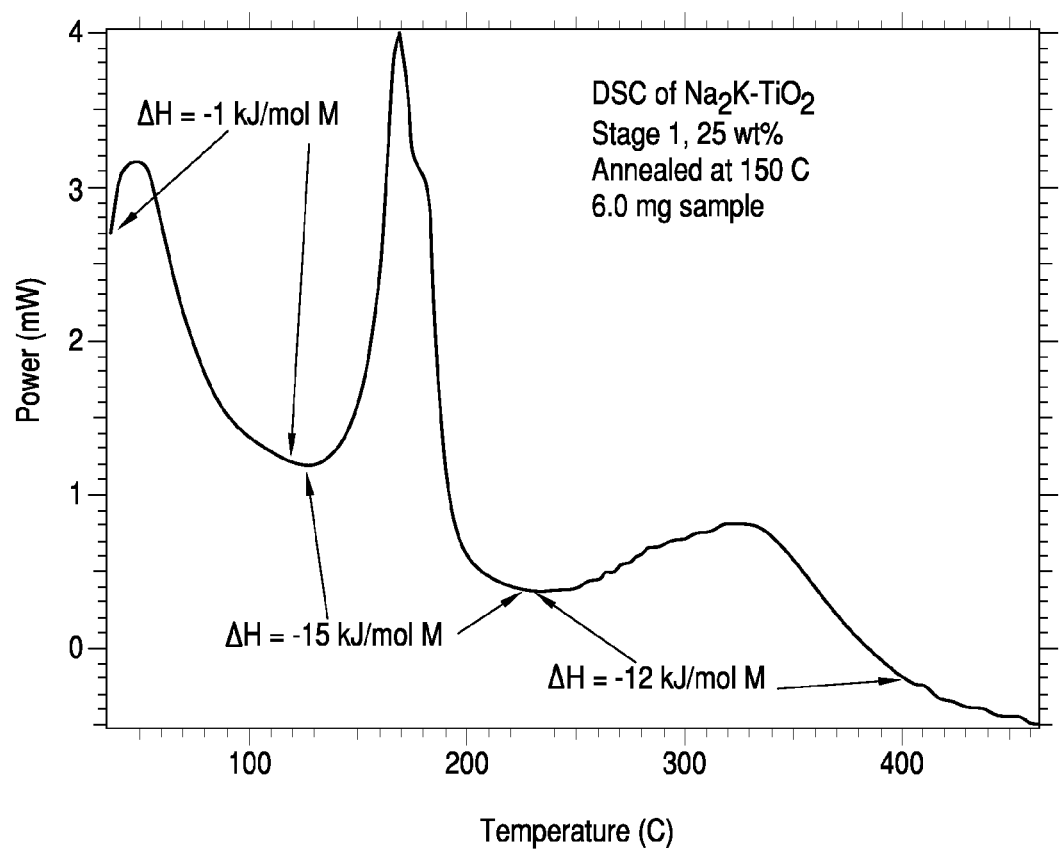
FIG. 4 shows a Differential Scanning Calorimetry (DSC) trace for a 6.0 mg sample of Stage I, 25 wt % $Na_2K$—$TiO_2$ that had been heated to 150° C. overnight.
Figure 5:
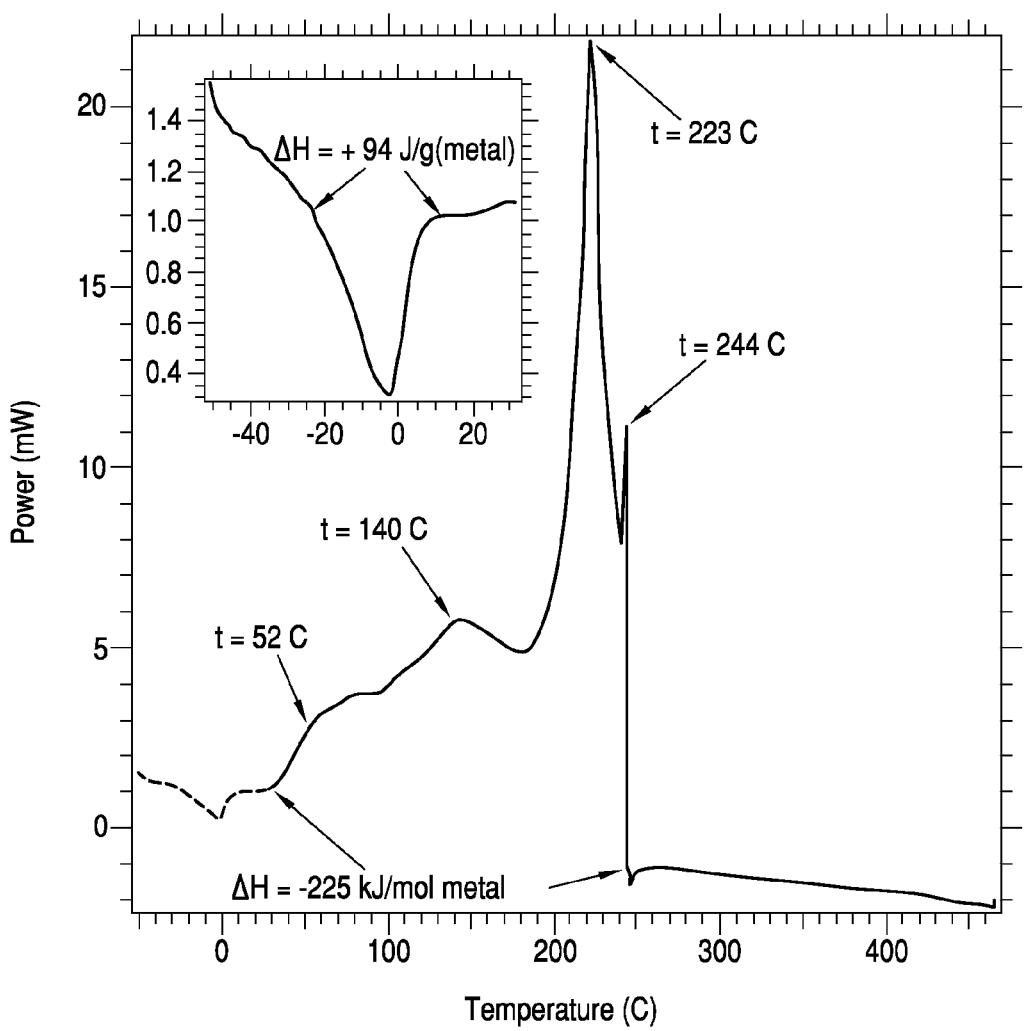
FIG. 5 shows a Differential Scanning Calorimetry (DSC) trace for an 11.7 mg sample of Stage 0, 25 wt % $Na_2K$—$Al_2O_3$, wherein the inset shows the melting endotherm of $Na_2K$ absorbed in the pores of the $Al_2O_3$.
Figure 6:
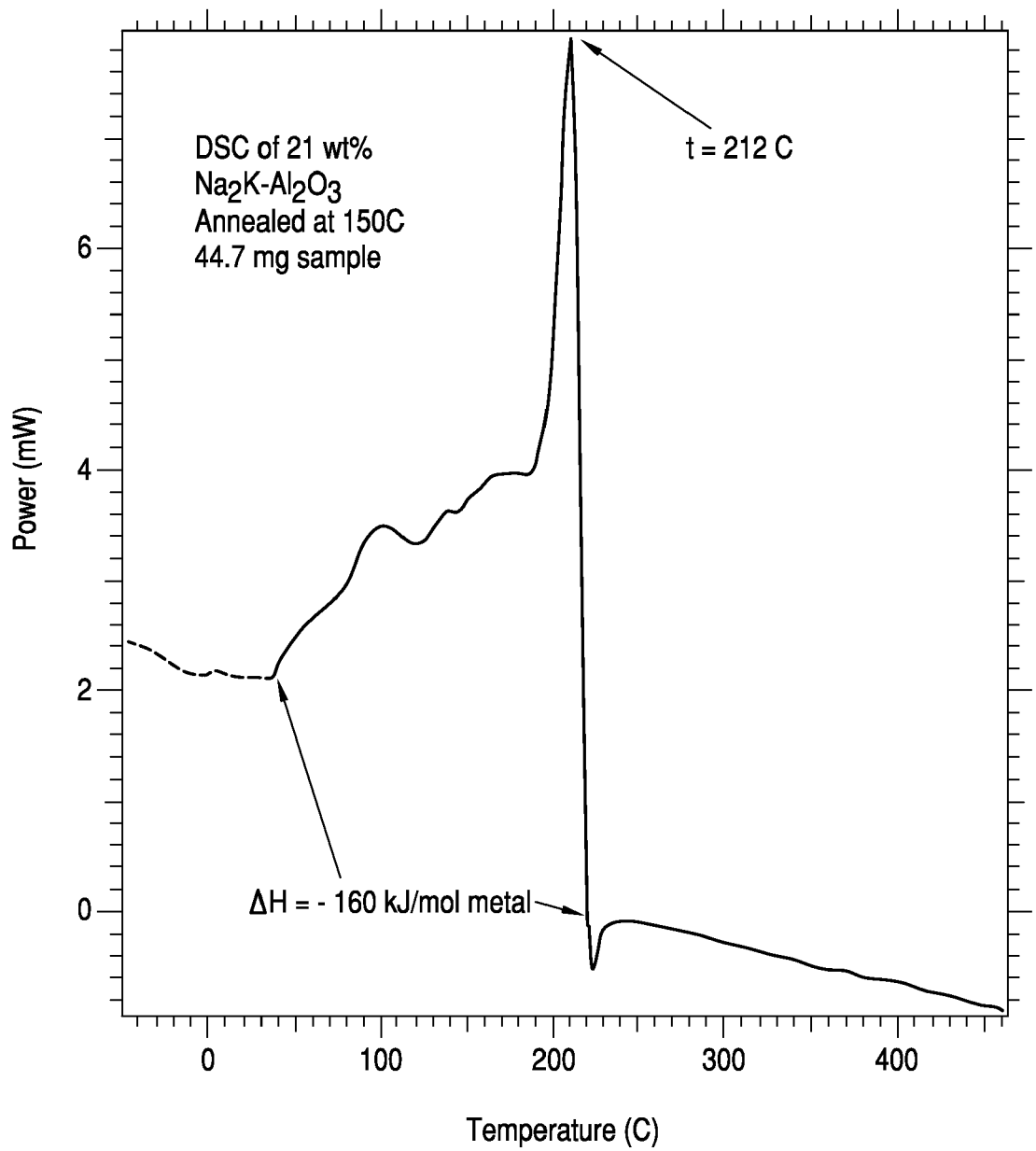
FIG. 6 shows a Differential Scanning Calorimetry (DSC) trace for a 44.7 mg sample of Stage I, 21 wt % $Na_2K$—$Al_2O_3$.
Figure 7:
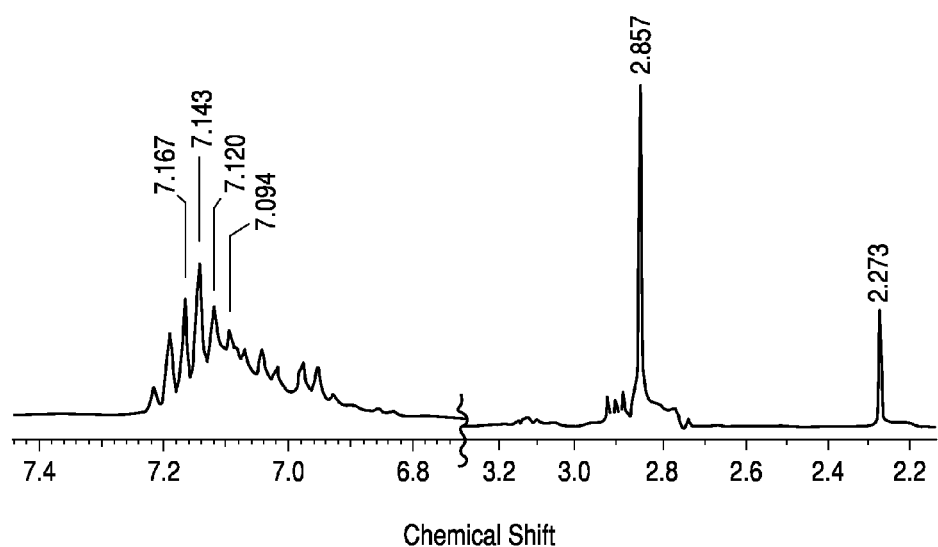
FIG. 7 shows the $^1H$ NMR spectrum of the product of reduction of benzyl chloride with Stage I, 25 wt % $Na_2K$—$Al_2O_3$, wherein the major product is bibenzyl and no benzyl chloride was detected in the product.

For example, FIG. 3 shows a Differential Scanning Calorimetry (DSC) trace for a 14.9 mg sample of Stage 0, 25 wt % Na$_2$K—TiO$_2$ prepared according to the procedure discussed in Example 2. Note the absence of a melting endotherm and the substantial exotherms as reaction between the metal and the TiO$_2$ occurs. FIG. 4 shows a Differential Scanning Calorimetry (DSC) trace for a 6.0 mg sample of Stage I, 25 wt % Na$_2$K—TiO$_2$ that had been heated to 150° C. overnight, as discussed in Example 2. FIG. 5 shows a Differential Scanning Calorimetry (DSC) trace for an 11.7 mg sample of Stage 0, 25 wt % Na$_2$K—Al$_2$O$_3$ prepared according to the procedure discussed in Example 1. The inset shows the melting endotherm of Na$_2$K absorbed in the pores of the Al$_2$O$_3$. Broad exotherms are also evident from 50-250° C. FIG. 6 shows a Differential Scanning Calorimetry (DSC) trace for a 44.7 mg sample of Stage I, 21 wt % Na$_2$K—Al$_2$O$_3$ prepared according to the procedure discussed in Example 3. Finally, FIG. 7 shows a $^1$H NMR spectrum of the product of reduction (with Stage I, 25 wt % Na$_2$K—Al$_2$O$_3$) of benzyl chloride in d-8 tetrahydrofuran (THF) prepared according to the procedure discussed in Example 5. The major product is bibenzyl. The aromatic region is on the left and the aliphatic region is on the right. The major peak of bibenzyl is at 2.86 ppm. The small peaks to the left are from THF and the small peak at 2.27 ppm is from the minor product, toluene.

Reaction Chemistry of the Group 1 Metal/Porous Metal Oxide Compositions

All Group 1 metal/porous metal oxide compositions of the invention react with water exothermically to produce hydrogen. Thus, advantageously, the compositions of the invention retain the reactivity of the Group 1 metal. Stage 0 material can be handled briefly in dry air, but it reacts slowly with oxygen and rapidly with moisture. By contrast, Stage I of the Group 1 metal/porous metal oxide compositions are unreactive towards dry oxygen. As shown in Example 6, the porous alumina yields recyclable alumina. Accordingly, the porous alumina yields an effective way to dry solvents by contacting the solvent with the porous alumina, thereby removing any water without consuming the porous alumina. This drying may be implemented either through a column or by a batch process.

Although the Stage I Group 1 metal/porous metal oxide compositions of the invention are relatively innocuous and not violently reactive, they do have a strong base present and form alkali metal hydroxides upon reaction with water. In contrast to the reaction products of silica gel-based materials that are completely soluble, the alumina based materials of the invention form a solid white reaction product that can be recycled merely by washing with water and re-calcining at 600° C. as shown in Example 6. The titanium oxide based materials of the invention form a black solid upon reaction with water.

Each stage of the Group 1 metal/porous metal oxide composition of the invention may be used as a reducing agent reacting with a number of reducible organic materials in the same manner known for alkali metals and their alloys. For example, the Group 1 metal/porous metal oxide compositions may be used to reduce aromatic compounds to their radical anions as is common in the so-called Birch reductions, commonly carried out with alkali metal—ammonia solutions. A Birch reduction is a general method of reduction of aromatic compounds by alkali metals in liquid ammonia. The theoretical and preparative aspects of the Birch reduction have been discussed in several reviews. (See, G. W. Watt, *Chem. Rev.*, 46, 317 (1950); A. J. Birch, *Quart. Rev.* (*London*), 4, 69 (1950); A. J. Birch and H. F. Smith, *Quart. Rev.* (*London*), 12, 17 (1958); and C. D. Gutsche and H. H. Peter, *Org. Syntheses*, Coll. Vol. 4, 887 (1963).). The Group 1 metal/porous metal oxide compositions of the invention readily form aromatic radical anions with both naphthalene and anthracene in tetrahydrofuran (THF) solutions. Thus, they could be substituted for the sodium in Birch reductions. Example 4 shows a reduction reaction that uses a Group 1 metal/porous metal oxide composition of the invention.

Similarly, violent reductions such as the Wurtz reduction of halogenated organic compounds such as PCB's might be carried out under controlled conditions. The Wurtz reaction is the coupling of two organic radicals (R) by treating two moles of the organic halides (RX) with two moles of sodium:

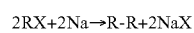

2RX+2Na→R-R+2NaX (See A. Wurtz, *Ann. Chim. Phys.* [3] 44, 275 (1855); *Ann.* 96, 364 (1855).; J. L. Wardell, *Comp. Organometal. Chem.* 1, 52 (1982); W. E. Lindsell, ibid. 193; B. J. Wakefield, ibid. 7, 45; D. C. Billington, *Comp. Org. Syn.* 3, 413-423 (1991).). The Group 1 metal/porous metal oxide compositions of the invention can be readily substituted for the sodium in a Wurtz reaction or other such dehalogentation reaction. Compositions of the invention have also been used to dehalogenate inorganic halides. Example 5 shows a Wurtz reduction using a Group 1 metal/porous metal oxide composition of the invention.

Use of the Group 1 metal/porous metal oxide compositions of the invention allow alkali metal reactions such as those described above to be carried out under safer conditions due to the safer handling of the compositions over the corresponding alkali metal or alloy. Use of the compositions also generally gives higher yields than the corresponding reaction with just the Group 1 metal.

Because Stage I material (such as a Stage I Na$_2$K/porous metal oxide composition) is very easy to prepare and retains much of the reducing ability of the parent Group 1 metal, it is likely to find use as a powerful and convenient reducing agent. Small glass columns filled with the Stage I powder are able to reduce a variety of organic compounds when they are dissolved in tetrahydrofuran (THF) and passed through the column. Alternatively, batch reactions can be carried out simply by stirring THF solutions of the organic compounds with the Stage I material. For example, as is shown below, benzophenone (1) is reduced to the radical anion (ketyl); and benzyl chloride (2) undergoes Wurtz reduction to form bibenzyl (3).

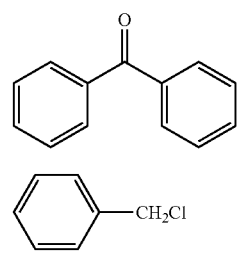

-continued

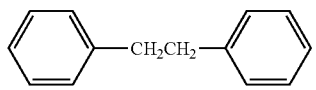

Numerous other reactions of Stage I materials are possible and likely. For example, they can reduce naphthalene to the radical anion and can convert benzyl chloride (2) to bibenzyl (3). The reduction of the representative compounds discussed above indicate that the Group 1 metal/porous metal oxide compositions of the invention can reduce aromatic compounds to the radical anions or dianions and completely dechlorinate aromatic chlorides. This material might therefore be able to destroy PCB's by dechlorination. The powerful reducing properties of the Group 1 metal/porous metal oxide compositions of the invention also permit the use of chromatographic columns packed with this material for the reduction of organic and inorganic compounds that are now reduced by Na—K or alkali metal-ammonia solutions.

A major use for both stages of reduced porous metal oxide compositions of the invention is in the fuel storage potential and the formation of hydrogen gas needed for mobile fuel cells. For example, large stocks of the reduced porous metal oxide powder might be kept on conveyor trays within a holding tank. Addition to water would liberate pure hydrogen gas plus water vapor. Both stages of reduced porous alumina produce near quantitative amounts of the hydrogen that would have been produced from the alkali metal used. The hydrogen could then be used to power mobile fuel cells. For example, stocks of the Group 1 metal/porous metal oxide compositions might be kept on conveyer trays within a holding tank. Water is then introduced and the mixing with the water would liberate hydrogen which can then be extracted and compressed or pressurized. The compressed hydrogen would be used to fill mobile fuel cells. The spent powder, at this stage is now just porous metal oxide that could be reactivated with new Group 1 metal or used for other purposes.

EXAMPLES

Example 1

Exemplary porous metal oxides. Porous $TiO_2$ (Anatase) from Sachtleben Chemie, (29.5 nm diameter pores, or 295 Å) and activated porous alumina (358 $m^2/g$) from Almatis AC were calcined in air at 600° C. and then cooled to room temperature. To these powders in a helium-filled glove box was added liquid $Na_2K$ dropwise onto the porous oxide in a stainless steel tray. The liquid alloy was quickly absorbed into the porous metal oxides. As long as the overall concentration of metal did not exceed 30 wt %, the white powder turned to dark black in color and the mixture became a uniform loose powder. This provided samples of Stage 0 material, as shown in FIG. 5.

Example 2

One significant feature of the Group 1 metal/porous metal oxide compositions of the invention is their ability to produce pure hydrogen gas upon addition to water. The "reducing power" of the Group 1 metal/porous metal oxide compositions was determined by adding water to an evacuated sample and collecting hydrogen with a modified Toeppler pump. The reducing power is defined as the weight percent of alkali metal or alloy used that would produce the same amount of hydrogen. This was verified by collecting the hydrogen produced from a known mass of material upon reaction with out-gassed water. The hydrogen was collected in a calibrated pipette using a modified Toeppler pump (mercury filled). Such analyses were run on every sample of reduced porous metal oxide, regardless of the stage of the material. For example, if a 30 wt % sample of NaK in Stage I porous metal oxide produced the same amount of hydrogen as would be produced by that amount of NaK alone, the reducing power would be 30%. The total amount of alkali metal hydroxide formed was then determined by the addition of HCl and back-titration with sodium hydroxide. The difference between the total alkali metal percentage as obtained from the titration and the reducing power is presumably a measure of the concentration of OH groups and other sources of hydrogen present on the porous metal oxide. Alkali metals can react with such groups during sample preparation to release hydrogen. This reaction is presumably the origin of the detectable amounts of gas formed during the mixing of the metal or alloy with the porous metal oxide. Except for the addition to porous $TiO_2$, the amount of hydrogen produced was generally within 90-95% of the amount that would have been produced by the metal(s) alone. When $Na_2K$—$TiO_2$ or Na—$TiO_2$ was used, the amount of hydrogen was reduced by an amount equivalent to about 10% metal. For example, a Stage 0 sample that was prepared with 25 wt % $Na_2K$ yielded hydrogen equivalent to only 13 wt % metal and another sample with 12 wt % metal yielded hydrogen equivalent to only 3 wt % $Na_2K$, as shown in FIG. 3. A sample of Stage I Na—$TiO_2$ made with 25 wt % Na yielded hydrogen equivalent to only 16 wt % metal. By contrast, a sample of Stage I $Na_2K$—$Al_2O_3$ with 30 wt % metal yielded hydrogen equivalent to 27 wt % metal. Even after exposure to dry air for two hours, the hydrogen yield corresponded to 23 wt % metal, indicating some reaction with air, but only moderate reactivity.

Example 3

The preparation of Stage I material can be performed by continuous heating of Stage 0 materials to 150° C. or by using the higher melting alkali metals, such as sodium and potassium. Outgassed and calcined porous alumina 14.0 g, was weighed out and, together with 6.0 g of Na metal, was introduced into a Parr Stainless steel reactor equipped with a Teflon gasket seal. The combination of porous metal oxide and Na was heated while rotating the reactor end-over-end at 60 rpm, first to 105° C. for 1 hr, then overnight at 155° C. The powder was loose, black and free flowing. Similar processes to convert Stage 0 $Na_2K$—$Al_2O_3$, $Na_2K$—$TiO_2$ and Na—$TiO_2$ to Stage I materials were also carried out. For example, a DSC of 21 wt % material is shown in FIG. 6.

Example 4

All of the alkali metal-porous metal oxide powders, whether Stage 0 or Stage I, are able to reduce naphthalene and anthracene to the corresponding radical anions The reduction was observed by the formation of an intense green or blue color of the solutions, respectively. These radical anions are stable enough to persist in solution for many hours. This reaction can be performed using several reaction setups, such as a batch reaction, or a chromatographic column loaded with the reducing material of the invention. The reaction with anthracene may be illustrated as is shown below.

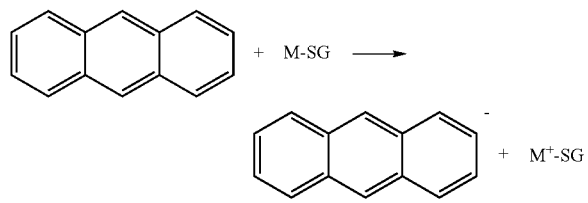

Example 5

One of the earliest reactions of alkali metals with organic compounds is the Wurtz reaction in which de-halogenation of a chlorocarbon results in coupling to form a new carbon-carbon bond. When used with a bulk alkali metal and the neat chlorocarbon however, the reaction can be dangerously explosive. As is shown below, this coupling reaction was carried out with benzyl chloride dissolved in THF by reduction with both Stage I $Na_2K$—$TiO_2$ and Stage I $Na_2K$—$Al_2O_3$ (~25 wt % $Na_2K$). The former was done by passage though a small column made from a Pasteur pipet and filled with the reducing material and the latter was done in a batch reaction. The only product detected by $^1H$ NMR was bibenzyl (See FIG. 7)

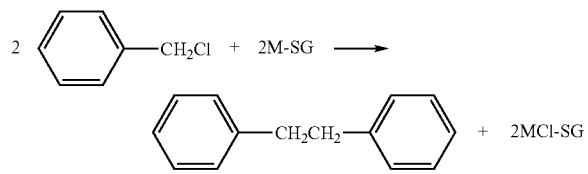

Example 6

To check the ability to recycle Stage I $Na_2K$—$Al_2O_3$, about 7.5 g of this material was reacted with water, resulting in the formation of copious amounts of a white residue. This was washed five times (with centrifugation each time) and dried. The dried powder was then calcined at 600° C. and brought into the helium-filled glove box. The recovered sample weighed 5.0 g and was combined drop-wise with 1.86 g of $Na_2K$ to form a loose black powder with a nominal metal concentration of 27.3 wt %. Hydrogen collection from this re-constituted $Na_2K$—$Al_2O_3$ yielded hydrogen equivalent to 20.8 wt % metal. Although the recovery procedure does not give 100% of the starting material, these results show that Stage I $Na_2K$—$Al_2O_3$ can be recycled by washing and calcinations. Thus, the same sample of $Al_2O_3$ could be re-used simply by washing, heat treatment, and re-introduction of alkali metals.

What is claimed is:

1. An alkali metal reduction of an organic compound, the improvement comprising contacting the organic compound with a Group 1 metal/porous metal oxide composition prepared by mixing a Group 1 metal in liquid form with a porous metal oxide selected from a group consisting of porous titanium oxide and porous alumina in an inert atmosphere under isothermal conditions sufficient to absorb the liquid Group 1 metal into the porous metal oxide pores, wherein the Group 1 metal/porous metal oxide composition produced reacts with dry $O_2$.

2. An alkali metal reduction of an organic compound, the improvement comprising contacting the organic compound with a Group 1 metal/porous metal oxide composition prepared by mixing a Group 1 metal in liquid form with a porous metal oxide selected from a group consisting of porous titanium oxide and porous alumina under exothermic conditions sufficient to absorb the liquid Group 1 metal into the porous metal oxide pores, wherein the Group 1 metal/porous metal oxide composition produced does not react with dry $O_2$.

3. An alkali metal reduction of an organic compound, the improvement comprising contacting the organic compound with a Group 1 metal/porous metal oxide composition prepared by mixing a Group 1 metal in liquid form with a porous metal oxide selected from a group consisting of porous titanium oxide and porous alumina under exothermic conditions sufficient to absorb the liquid Group 1 metal into the porous metal oxide pores and heating the resulting mixture to a temperature of at least 150° C., wherein the Group 1 metal/porous metal oxide composition produced does not react with dry $O_2$.

4. The alkali metal reduction of an organic compound of any of claims 1, 2, or 3, wherein the reduction reaction is a dehalogenation reaction of a halogenated organic compound.

5. The alkali metal reduction of an organic compound of any of claims 1, 2, or 3, wherein the reduction reaction is a Wurtz reaction of a halogenated organic compound.

6. The alkali metal reduction of an organic compound of any of claims 1, 2, or 3, wherein the pores of the porous metal oxide have an average pore size of approximately 50 to 1,000 Å.

7. The alkali metal reduction of an organic compound of any of claims 1, 2, or 3, wherein the Group 1 metal is selected from the group consisting of sodium, potassium, rubidium, cesium, and an alloy of two or more Group 1 metals thereof.

8. The alkali metal reduction of an organic compound of claim 1, wherein the mixing of the liquid Group 1 metal and the porous metal oxide selected from porous titanium oxide and porous alumina occurs at ambient temperature.

9. The alkali metal reduction of an organic compound of any of claims 2 or 3, wherein the Group 1 metal is present in an amount up to 30% by weight.

10. A method of producing hydrogen gas comprising:
contacting a Group 1 metal/porous metal oxide composition with water,
wherein the Group 1 metal/porous metal oxide composition is prepared by mixing a Group 1 metal in liquid form with a porous metal oxide selected from a group consisting of porous titanium oxide and porous alumina in an inert atmosphere under isothermal conditions sufficient to absorb the liquid Group 1 metal into the porous metal oxide pores, wherein the Group 1 metal/porous metal oxide composition produced reacts with dry $O_2$.

11. A method of producing hydrogen gas comprising:
contacting a Group 1 metal/porous metal oxide composition with water,
wherein the Group 1 metal/porous metal oxide composition is prepared by mixing a Group 1 metal in liquid form with a porous metal oxide selected from a group consisting of porous titanium oxide and porous alumina under exothermic conditions sufficient to absorb the liquid Group 1 metal into the porous metal oxide pores, wherein the Group 1 metal/porous metal oxide composition produced does not react with dry $O_2$.

12. A method of producing hydrogen gas comprising:
contacting a Group 1 metal/porous metal oxide composition with water, wherein the Group 1 metal/porous metal oxide composition is prepared by mixing a Group 1 metal in liquid form with a porous metal oxide selected from a group consisting of porous titanium oxide and porous alumina under exothermic conditions sufficient to absorb the liquid Group 1 metal into the porous metal oxide pores and heating the resulting mixture to a temperature of at least 150° C., wherein the Group 1 metal/porous metal oxide composition produced does not react with dry $O_2$.

* * * * *